United States Patent [19]

Schneider

[11] Patent Number: 4,806,656
[45] Date of Patent: Feb. 21, 1989

[54] PREPARATION OF N-THIENYL-CHLOROACETAMIDES AND TETRAHYDRO-THIEN-3-YLIDENIMINES

[75] Inventor: Hermann Schneider, Grenzach-Wyhlen, Fed. Rep. of Germany

[73] Assignee: Sandoz Ltd., Basel, Switzerland

[21] Appl. No.: 762,333

[22] Filed: Aug. 5, 1985

[51] Int. Cl.$^4$ .................. C07D 333/36; C07D 333/42
[52] U.S. Cl. ......................... 549/69; 549/68
[58] Field of Search .............................. 549/77, 68, 69

[56] References Cited

U.S. PATENT DOCUMENTS

| | | | |
|---|---|---|---|
| 3,901,917 | 8/1975 | Richter et al. | 549/77 |
| 4,239,897 | 12/1980 | Rossy et al. | 549/61 |
| 4,242,518 | 12/1980 | Rossy et al. | 549/61 |
| 4,666,502 | 5/1987 | Seckinger et al. | 71/90 |

FOREIGN PATENT DOCUMENTS 37066 4/1966 Ireland .

OTHER PUBLICATIONS

Coffey Rodd's Chemistry of Carbon Compounds vol. IV Het Comp.–Part A 2nd ed. p. 258.

Weininger Contemporary Org. Chem. 1972 pp. 259–260.
Thiophene and its Derivatives, Part One, ed. by Salo Gronowitz, Interscience Publication, John Wiley & Sons, 1985, pp. 160–161, 203, 200 and 210.

Primary Examiner—Alan Siegel
Attorney, Agent, or Firm—Gerald D. Sharkin; Richard E. Vila

[57] ABSTRACT

The invention provides compounds of formula I

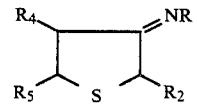

wherein
R is $C_{1-4}$alkoxy-$C_{2-4}$alkyl of which the $C_{1-4}$alkoxy group is separated by at least 2 C-atoms from the N-atom to which R is bound,
each of $R_2$ and $R_4$ independently is $CH_3$ or $C_2H_5$ and $R_5$ is H or $CH_3$, the preparation of such compounds and the use of such compounds for the preparation of N-(thien-3-yl)-chloroacetamides.

4 Claims, No Drawings

PREPARATION OF N-THIENYL-CHLOROACETAMIDES AND TETRAHYDRO-THIEN-3-YLIDENIMINES

The present invention relates to novel tetrahydrothien-3-ylidenimines, their preparation and the use of such imines for the production of N-thienyl-chloroacetamides.

More specifically, the invention provides novel tetrahydrothiophenimines of formula I

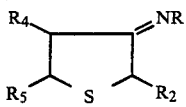

wherein

R is $C_{1-4}$alkoxy-$C_{2-4}$alkyl of which the $C_{1-4}$alkoxy group is separated by at least 2 C-atoms from the N-atom to which R is bound,
each of $R_2$ and $R_4$ independently is $CH_3$ or $C_2H_5$ and $R_5$ is H or $CH_3$.

It has been found that compounds of formula I can be readily dehydrogenated to compounds of formula II

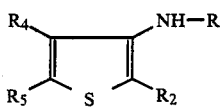

wherein R, $R_2$, $R_4$ and $R_5$ are as defined above.

Compounds of formula II are known intermediates for the preparation of compounds of formula III

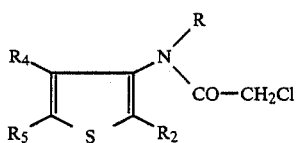

wherein R, $R_2$, $R_4$ and $R_5$ are as defined above.

Compounds of formula III are known herbicides.

Compounds II and III are disclosed in UK Patent Specification 2 114 566A. Said specification discloses several processes for the preparation of compounds of formula III, but none of the processes disclosed therein, or in other literature, allows the production of the compounds of formula III starting from readily available starting materials.

The present invention discloses a very convenient route for the production of compounds of formula III.

One aspect of the invention is the preparation of a compound of formula II by dehydrogenation of a compound of formula I.

Said dehydrogenation may be effected catalytically or by oxydation with oxygen or with oxydation agents such as sulphur, sulphurylchloride and thionylchloride; it is preferably effected catalytically or with thionylchloride as oxydation agent. Particularly thionylchloride has been found surprisingly suitable for the dehydrogenation of compounds of formula I.

The catalytical dehydrogenation of a compound of formula I can be effected in the presence of any dehydrogenation catalyst. Examples of known dehydrogenation catalysts suitable for use in the dehydrogenation reaction of the invention are noble metals such as Pt or Pd, or other metals such as $Cr_2O_3$ or mixtures thereof with other metals such as CuO. The catalytical dehydrogenation can be carried out under the conditions known for such reactions. Where for example the catalyst is Pt, it is conveniently finely distributed on a carrier such as charcoal (e.g. 5% Pt/C). The dehydrogenation reaction is then suitably carried out with heating, preferably at a temperature above 180° C., e.g. at 220° C. or higher temperature, and under an inert gas atmosphere, such as a $N_2$ blanket.

Compounds of formula I react—even below room temperature with oxygen to form an intermediate product which decomposes on heating, usually at a temperature of ca. 100° C. or higher, to compounds of formula II. This conversion is conveniently performed in one step by oxydation above the decomposition point in a suitable solvent, e.g. an aromatic solvent such as toluene under reflux.

When applying an oxydation agent, the oxydation step is conveniently effected in a solvent which is inert under the reaction conditions. Examples of suitable solvents are chlorinated hydrocarbons, such as $CH_2Cl_2$ and hydrocarbons such as toluene or cyclohexane. Where the oxydation agent is sulphur, the oxydation reaction is suitably carried out with heating; where the oxydation agent is sulphuryl chloride or thionylchloride the reaction temperature is conveniently in the range of from $-30°$ C. to $+80°$ C., e.g. at room temperature (about 20° C. to 30° C.).

Thionylchloride is surprisingly suitable for use as oxydation agent in this reaction: the reaction can be carried out under mild reaction conditions and undesired side reactions (such as chlorination, further oxydation etc.) are not observed.

The thus obtained compounds of formula II are converted to compounds of formula III by N-chloroacetylation. Said N-chloroacetylation may be carried out according to procedures known for the preparation of chloroacetamides from the corresponding amines, e.g. under the conditions disclosed in UK Patent Specification 2 114 566A.

Where the compounds of formula I are oxydized with the aid of sulphurylchloride or thionylchloride, the compounds of formula II will be obtained in the form of the hydrochloride acid addition salt. Said hydrochloride can be reacted with chloroacetylchloride without prior isolation from the reaction mixture, and in the absence of a base, giving practically quantitative yields of compounds of formula III.

The compounds of formula I are readily obtained from the corresponding tetrahydrothiophen-3-ones of formula IV

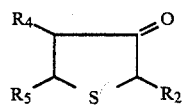

wherein $R_2$, $R_4$ and $R_5$ are as defined above, by reaction with an amine of formula V $$H_2N-R \qquad (V)$$

wherein R is as defined above.

Such condensation reaction is conveniently effected in a solvent which is inert under the reaction conditions, such as cyclohexane or toluene. The reaction is preferably carried out with heating, e.g. at reflux temperature. The reaction product is suitably dried e.g. with the aid of a water trap or by an appropriate molecular sieve, e.g. of 5 Å. This may be done continuously, by using a cooler, e.g. a water cooler, and directing the condensate through a column comprising a molecular sieve, which is preferably protected by $N_2$ to exclude atmospheric oxygen.

The above disclosed reaction route for the preparation of compounds of formula III from compounds of formula IV—via compounds of formula I and II may be effected in one and the same reaction vessel, i.e. compounds of formula I and II may be obtained in good yields and need not be isolated from the reaction vessel for the next reaction step.

Compounds of formula IV are novel. They are readily obtained by cyclisation of compounds of formula VI

HOCO—CH(R$_2$)—S—CH(R$_5$)—CH(R$_4$)COOH    (VI)

wherein R$_2$, R$_4$ and R$_5$ are as defined above.

Such cyclisation can be carried out under the conditions of a Ruzicka cyclisation or modifications thereof.

The cyclisation is conveniently effected with heating; the presence of a condensation agent, such as Ba(OH)$_2$, MnCO$_3$, Fe powder, acetates of Fe, CO(II) or Ni(II), acetic acid anhydride/LiCl or a tertiary amine e.g. a trialkylamine, promotes cyclisation. The use of Fe powder or of acetates of Fe, CO(II) or Ni(II) as condensation agent is particularly advantageous.

The term acetates of Fe as used herein is intended to comprise Fe(II) and Fe(III) acetate compounds such as Fe(acetate)$_2$ and Fe(OH)$_2$-(acetate).

Compounds of formula VI are also novel. They may be obtained from readily obtainable starting materials by addition reaction of a compound of formula VII

HO—CO—CH(R$_2$)—SH    (VII)

wherein R$_2$ is as defined above, to a compound of formula VIII

R$_5$—CH=C(R$_4$)—COOH    (VIII)

wherein R$_4$ and R$_5$ are as defined above.

The addition of a compound of formula VII to a compound of formula VIII is conveniently effected under the conditions of a Michael addition or modifications thereof. The addition is conveniently effected with heating. The compound of formula VII may be used for example in its salt form (carboxylate salt), e.g. alkali metal salt form such as the Na carboxylate form. The compound of formula VII may however also be used in its free acid form, in which case the addition is conveniently effected in the presence of a tertiary amine, e.g. a trialkylamine such as tri(n-butyl)amine or of an acetate of Fe, CO(II) or Ni(II). The latter process variante can be carried out in the absence of a solvent, the reaction proceeds fast with high yields, nonreacted starting material may be recovered and the compounds of formula VI may be cyclisized to compounds of formula IV without necessitating the isolation of the compounds of formula VI.

R$_2$ is preferably CH$_3$. R$_4$ is preferably CH$_3$. R$_5$ is preferably H. R signifies preferably CH(CH$_3$)CH$_2$OCH$_3$, CH$_2$CH$_2$—O—nC$_3$H$_7$ or CH$_2$CH$_2$—O—iC$_3$H$_7$, more preferably CH(CH$_3$)—CH$_2$—OCH$_3$.

The following examples illustrate the invention. Temperatures are given in centigrade.

EXAMPLE

N-(1-Methoxyprop-2-yl)-2,4-dimethyltetrahydrothien-3-ylidenimine

A reaction flask is fitted with a thermometer, a water cooler and a column charged with 31 g molecular sieve (5 Å).

A reaction flask is charged with a mixture of 0.2 mol of 2,4-dimethyltetrahydrothiophen-3-one, 0.225 mol of 1-methoxy-2-aminopropane and 50 ml of cyclohexane. The reaction flask is fitted with a thermometer a water cooler and a column charged with 31 g molecular sieve (5 Å) in such a way, that the condensate of the boiling reaction mixture is directed continuously through the molecular sieve. The apparatus is protected by $N_2$ to exclude atmospheric oxygen. The reaction mixture is boiled during 9 hours. The title compounds is then vacuum distilled at 0.5 Torr at the boiling range of 65°–80°.

EXAMPLE 2

N-(1-Methoxyprop-2-yl)-2,4-dimethyl-3-aminothiophene 0.1 Mol thionylchloride dissolved in 20 ml toluene are added dropwise with stirring and cooling at 10°–20° to a solution of 0.1 mol N-(1-methoxyprop-2-yl)-2,4-dimethyltetrahydrothien-3-ylidenimine in 80 ml.

The reaction mixture is stirred for 1 hour and then rendered alkaline with a conc. solution of caustic soda. The aqueous phase is separated off, the organic phase washed with water, dried and the toluene distilled off in vacuum. The residue is distilled at 0.2 Torr and yields the title compound, b.p. 70°–72°.

EXAMPLE 3

N-(-1-Methoxyprop-2-yl)-2,4-dimethylaminothiophene 0.01 Mol N-(1-methoxyprop-2-yl)-2,4-dimethyltetrahydrothien-3-ylidenimine are added dropwise, within 5 minutes to 0.013 mol sulphur powder in 2 ml boiling toluene (under reflux). The mixture is stirred under reflux for another 5 minutes and the crude residue distilled in a bulb tube, at 0.5 Torr and 150°–170°, whereby the title compound is obtained as a clear distillate.

EXAMPLE 4

N-(1-Methoxyprop-2-yl)-2,4-dimethylaminothiophene 0.1 Mol N-(1-methoxyprop-2-yl)-2,4-dimethyltetrahydrothien-3-ylidenimine are heated under $N_2$ atmosphere with 2 g 5% Pt/charcoal at 200°, during 11 hours. The catalyst is filtered off and the filtrate distilled at 0.1 Torr. The title compound is obtained at the boiling range of 68°–71°.

EXAMPLE 5

N-(2,4-Dimethylthien-3-yl)-N-(1-methoxyprop-2-yl)-chloroacetamide (a) Involving use of compound of formula II in salt form 0.02 Mol thionylchloride in 5 ml toluene are added dropwise, within 40 minutes, to 0.02 mol N-(1-methoxyprop-2-yl-)-2,4-dimethyltetrahydrothien-3-ylidenimine, dissolved in 10 ml of toluene at 20°. The reaction mixture is stirred for 2 hours whereby the hydrochloride of N-(-1-methoxyprop-2-yl)-2,4-dimethyl-3-aminothiophene is obtained. Then are added 0.02 mol of chloroacetylchloride dissolved in 5 ml toluene. This mixture is heated during 1 hour at reflux, whereby HCl escapes. The title compound is obtained by column chromatography on silica gel with cyclohexane/ethyl acetate (8:2), b.p. 148°–150°/0.03 Torr.

(b) Involving use of a compound of formula II in base form.

To a mixture of 315 g (1.58 mol) N-(1-methyl-2-methoxy-ethyl)2,4-dimethyl-3-aminothiophene in 1500 ml $CH_2Cl$ and 240 g (1.75 mol) of $K_2CO_3$ in 250 ml $H_2O$ are added dropwise, at room temperature, and while stirring vigorously, 200 g (1.77 mol) of chloroacetylchloride. After half an hour's reaction time at room temperature, the organic phase is separated off, washed with water (2×200 ml), dried over $Na_2SO_4$ and concentrated by evaporation.

The title compounds is obtained by chromatography on silica gel with hexane/diethylether 85:15.Rf =0.3 (silica gel; diethylether/hexane 2:1) b.p. 148°–150°/0.03 Torr.

EXAMPLE 6

2,4-Dimethyltetrahydrothiophen-3-one

-Cyclisation of 2,5-dimethyl-3-thiaadipic acid (a) With Fe powder

100 Parts of 2,5-Dimethyl-3-thiaadipic acid are heated at 180°–220° with 7.5 parts of iron powder. The thus obtained distillate is dissolved in $CH_2Cl_2$, washed with saturated aqueous $NaHCO_3$ solution, dried over $Na_2SO_4$. The title compound is distilled at 2 Torr, at a temperature of 39°–40°.

(b) With Ba$(OH)_2$.

A mixture of 0.94 mol of 2,5-dimethyl-3-thiaadipic acid and 10 g of Ba(OH)$_2$ is heated during 24 hours in a distillation flask, at 230°–250°, with stirring. The distillate is extracted with diethylether, the ether solution dried (over $MgSO_4$) and distilled under reduced pressure b.p. 39°–40° at 2 Torr.

(c) With acetic acid anhydride.

0.5 Mol of 2,5-thiaadipic acid, 300 ml of acetic acid anhydride and 4 g LiCl is stirred for 6 hours at 120°. The crude mixture is poured onto ice, and 10 cm$^3$ $H_2SO_4$ conc. are added thereto. The mixture is then stirred overnight, rendered alkaline with conc. NaOH solution, while cooling with pieces of ice, and extracted several times with diethylether. The ether phase is washed with water, dried over $MgSO_4$ and concentrated by evaporation. The residue is distilled over a Vigreux column to give the title compound b.p. 81°–88° at 20 Torr.

EXAMPLE 7

2,5-Dimethyl-3-thiaadipic acid

To a solution of 320 g (8 mol) NaOH in 1300 ml water are added within 15 minutes, 424 g (4 mol) of thiolactic acid. After decay of the exothermic reaction (35°) are added 344 g (4 mol) of methacrylic acid and the reaction mixture is then stirred for 18 hours at 80°.

The mixture is cooled to 50°, poured onto a mixture of 3 kg of ice and 750 ml of concentrated HCl and extracted with 4 1000 ml portions of $CH_2Cl_2$. The $CH_2Cl_2$ extracts are dried with $Na_2SO_4$ and the organic phase then concentrated by rotary flash evaporation, yielding the title compound of m.p. 78°–80° in the form of colourless crystals.

EXAMPLE 8

2,5-Dimethyltetrahydrothiophen-3-on (a) With tertiary amine

To a mixture of 0.2 mol thiolactic acid and 0.2 mol methacrylic acid are added dropwise 0.2 mol tributylamine, whereby the reaction temperature rises up to 60°. The reaction mixture is then heated for 1 hour at 150°–160° and thereafter at 210°–220°. Under these conditions distills a mixture of the title compound, water and tributylamine at 150°–170° over, which is dissolved in ethyl acetate, diluted with water and neutralised with 10% HCl. The organic phase is extracted with 2N NaOH, washed neutral, dried and concentrated by evaporation. The residue is distilled at 15 Torr, yielding the title compound at the boiling range of 70°–73°.

(b) With Fe(II) acetate

A mixture of 85.9 g thiolactic acid, 70.0 g methacrylic acid and 0.8 g Fe acetate is stirred and heated to 150°–160° for 1 hour. Then another 0.8 g Fe acetate are added and the temperature is raised to 200°–210° C. for 2 hours to yield 103.9 g of a distillate. This is dissolved in 200 ml cyclohexane, made alkaline with sodium hydroxide and separated in a separation funnel. The aqueous phase is extracted with 100 ml cyclohexane. The combined organic layers are washed with water, dried over $MgSO_4$ and evaporated at 15 Torr to yield the title compound.

The aqueous layer is acidified with hydrochloric acid and extracted with methylenechloride. The extract is washed with water, dried with $MgSO_4$, evaporated at 15 Torr to yield 10.6 g of a mixture of methacrylic acid and thiolactic acid in the ratio 2:1.

EXAMPLE 9

N-(1-methoxyprop-2-yl)-2,4dimethyl-3-aminothiophene

A solution of 2 g (0.01 mol) N-(1-methoxyprop-2-yl)-2,4-dimethyltetrahydrothien-3-ylidenimine in 3 g carbon tetrachloride is stirred for 1 hour at room temperature under an atmosphere of oxygen. 200 ml of $O_2$ are consumed. The NMR-spectrum of the solution shows no signals for aromatic protons. Then the product is distilled in a bulb tube at 0.2 Torr and 150°–180° air temperature to yield the title compound.

I claim:

1. The process for the preparation of a compound of the formula II

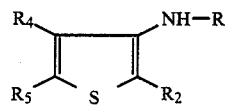

in hydrochloride acid addition salt form, wherein R is $C_{1-4}$alkoxy-$C_{2-4}$alkyl of which the $C_{1-4}$alkoxy group is separated by at least 2 carbon atoms from the N-atom to which R is bound, each of $R_2$ and $R_4$ independently is $CH_3$ or $C_2H_5$ and $R_5$ is H or $CH_3$, comprising reacting a compound of the formula I

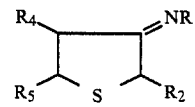

wherein R, R₂, R₄ and R₅ are as above defined, with thionylchloride in an inert solvent at a temperature in the range of from minus 30° C. to plus 80° C.

2. The process for the preparation of a compound of the formula III

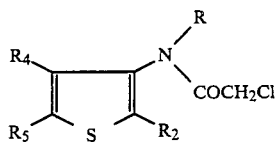

wherein R is $C_{1-4}$alkoxy-$C_{2-4}$alkyl of which the $C_{1-4}$alkoxy group is separated by at least 2 carbon atoms from the N-atom to which R is bound, each of R₂ and R₄ independently is CH₂ or C₂H₅ and R₅ is H or CH₃, comprising reacting a compound of the formula I

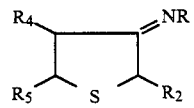

wherein R, R₂, R₄ and R₅ are as above defined, with thionylchloride in an inert solvent at a temperature in the range of from minus 30° C. to plus 80° C. to obtain a compound of the formula II

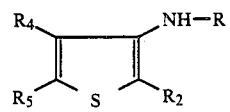

in hydrochloride acid addition salt form wherein R, R₂, R₄ and R₅ are as above defined, maintaining said acid addition said form of the compound of the formula II in the inert solvent in which it was formed and reacting said acid addition salt form in said inert solvent with chloroacetylchloride in the absence of a base to form said compound of the formula III.

3. The process of claim 2 in which the inert solvent is a hydrocarbon or chlorinated hdrocarbon solvent.

4. The process of claim 2 in which R is 1-methoxy-prop-2-yl, R₂ and R₄ are each methyl and R₅ is H.

* * * * *